United States Patent [19]

Ueno et al.

[11] Patent Number: 4,556,389
[45] Date of Patent: Dec. 3, 1985

[54] METHOD AND COMPOSITIONS FOR BONDING METALS AND CERAMICS WITH WHICH TO MAKE PROSTHETIC TEETH

[75] Inventors: Masato Ueno; Masayoshi Sato; Mitsuyuki Tasaka; Tatsuro Naito, all of Hiroshima, Japan

[73] Assignees: Four Brain Company Ltd., Hiroshima; Kyoto Ceramic Company Ltd., Kyoto, both of Japan

[21] Appl. No.: 336,423

[22] Filed: Dec. 31, 1981

[51] Int. Cl.⁴ .............................................. A61C 5/08
[52] U.S. Cl. ................... 433/206; 106/1.12; 264/19; 427/404; 427/405; 427/419.4; 428/325; 428/450; 428/469; 433/208; 433/223; 433/207
[58] Field of Search ............ 433/212, 222, 223, 202, 433/206, 208; 264/19; 523/109; 106/1.12; 428/325, 450, 469; 427/404, 405, 419.4

[56] References Cited

U.S. PATENT DOCUMENTS

| | | | |
|---|---|---|---|
| 3,049,437 | 8/1962 | Rejdak | 106/1.12 |
| 3,395,027 | 7/1968 | Klotz | 106/1.12 |
| 3,835,066 | 9/1974 | Davies | 106/1.12 |
| 3,934,348 | 1/1976 | Janjic | 433/223 |
| 4,104,798 | 8/1978 | Takahashi | 433/222 |

FOREIGN PATENT DOCUMENTS

| | | | |
|---|---|---|---|
| 5313591 | 2/1978 | Japan | 433/222 |
| 5316494 | 2/1978 | Japan | 433/222 |

Primary Examiner—Ellis P. Robinson
Attorney, Agent, or Firm—Spensley Horn Jubas & Lubitz

[57] ABSTRACT

A novel method for firmly bonding metal and ceramics comprising the steps of applying a composite plating composition consisting of a metal containing plating solution and fine particles of ceramic on a surface of metal to which the ceramic is to be bonded, thereby forming a metal plating layer on the surface having partially projected fine particles of ceramic, and then firing the coated metal in order to fuse the ceramic thereto.

9 Claims, 8 Drawing Figures

 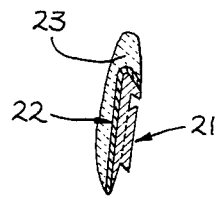 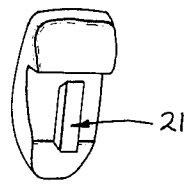
FIG.5(a)  FIG.5(b)  FIG.5(c)
 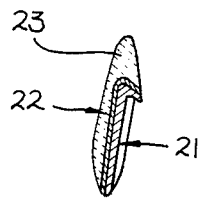 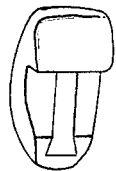
FIG.6(a)  FIG.6(b)  FIG.6(c)
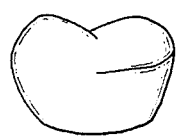 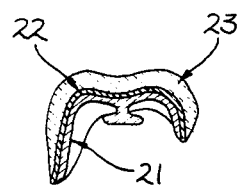 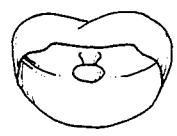
FIG.7(a)  FIG.7(b)  FIG.7(c)
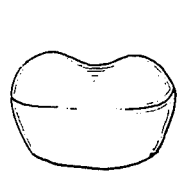 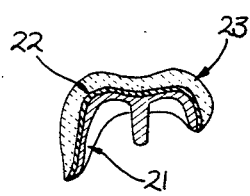 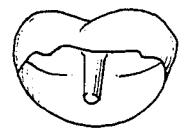
FIG.8(a)  FIG.8(b)  FIG.8(c)

METHOD AND COMPOSITIONS FOR BONDING METALS AND CERAMICS WITH WHICH TO MAKE PROSTHETIC TEETH

BACKGROUND OF THE INVENTION

1. Field of the Invention

This invention relates to a method of firmly bonding metal and ceramics, prosthetic teeth produced by the application of such method and composite plating materials used in such bonding method.

2. Description of the Prior Art

In the past, ceramics were directly coated on the surface of metal and then fired to fuse them. However, because this method attained only poor bonding strength, another method is generally employed in which the surface of the metal is first roughened by etching. Then the ceramic is fired onto the roughened surface so as to cause the ceramic to base. In this manner one is able to obtain higher bonding strength. This method also has disadvantages in that sufficiently high bonding strength can not be obtained because of the great difference in the physical properties between metal and ceramics, and further because the ceramics can be separated from their bonded position by small stresses.

Accordingly, these conventional methods cannot be used when the bonded products are thereafter subjected to severe vibration, repeated heating and cooling or excessive load. Thus, these methods have had only restricted fields of application and even then are not reliable.

A method of producing prosthetic teeth, especially cast metal crowns fused to porcelain, which is conventionally used in the dental field, comprises coating cast metal crowns with opaque porcelain and then with dental crown colored porcelain, in order to hide the color of the metal and to improve the bonding to the dental crown colored porcelain in the upper layer. The coated crown is then fired. However, this method also has the problem of weak bonding of the metal crowns to opaque porcelain. One is now also forced to use a nickel-chromium alloy due to a rise in prices and a shortage of non-oxidizable noble metals such as gold or palladium which are ideal as a material for the cast metal crowns. When the opaque porcelain coated on a nickel-chromium alloy is fired at a temperature ranging from 940° C. to 960° C., the alloy is oxidized and gas is evolved. It is believed that the gas remains within the opaque porcelain such that firm bonding can not be obtained and defects such as break-away and discoloration of the opaque porcelain occur.

In order to eliminate these defects, a non-oxidizable metal such as gold, palladium, nickel, chromium and the like could be plated on the surface of the cast metal crown of nickel-cromium alloy. Only by plating the non-oxidizable metal, however, can the surface of the cast metal crown be prevented from the oxidation. In such a method, however, the inorganic opaque porcelain is not firmly bonded.

Thus, it is an object of this invention to provide a novel method of firmly bonding metal and ceramics.

It is another object of this invention to provide composite plating materials used for firmly bonding metal and ceramics.

It is still another object of this invention to provide prosthetic teeth in which porcelain is firmly bonded to metal crowns such that it cannot be easily broken away and/or discolored.

SUMMARY OF THE INVENTION

This invention provides a novel method of firmly bonding metal and ceramics. The method uses a composite plating composition comprising a metal plating solution having fine particles of ceramics dispersed therein. The composition is applied by plating to a metal surface to which the ceramics are to be bonded, thereby forming a metal plating layer on the surface having partially projected fine ceramic particles. A layer of ceramics to be bonded is formed on the metal plating layer and then fired so as to bond the ceramics thereto by fusion.

This invention provides, in another aspect, composite primary materials consisting of a metal plating solution incorporated with fine particles of ceramics for use in a method of bonding metal and ceramics.

This invention also provides prosthetic teeth produced by plating a composite plating material consisting of a metal plating solution incorporated with fine particles of ceramics on the surface of a metal crown for prosthetic teeth, thereby forming a metal plating layer on the surface which has partially projected fine particles of the ceramics. Dental opaque porcelain is then fired on the surface of the metal plating layer to fuse them together.

The novel features which are believed to be characteristic of the invention, both as to its organization and method of operation, together with further objectives and advantages thereof, will be better understood from the following description considered in connection with accompanying drawings in which a presently preferred embodiment of the invention is illustrated by way of example. It is to be expressly understood, however, that the drawings are for the purpose of illustration and description only and not intended as a definition of the limits of the invention.

DETAILED DESCRIPTION OF THE PREFERRED EMBODIMENT

A method of bonding metal and ceramics according to this invention will now be more specifically described by the aid of the accompanying drawings.

Figure 1:
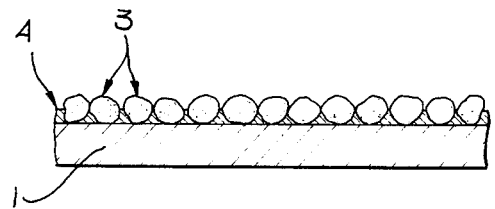
FIG. 1 is an enlarged cross-sectional view of the metal base having thereon a metal plating layer on the surface of which has partially projected fine particles of ceramic.

As shown in FIG. 1, on the surface of the metal base 1, e.g., an iron base, to be bonded to the ceramic, there is a metal plating 4. Layer 4 is formed by plating a composite plating composition comprising a metal plating solution incorporated with fine ceramic particles 3. Such plating methodology is well known in the art and will not be discussed in detail herein. By plating the composition, the fine ceramic particles 3 are fixed in the metal plating layer 4, but partially project above the surface.

Layer 4 can be made utilizing well known plating solutions from which a metal such as nickel, chromium, gold, palladium, etc. or an alloy such as nickel-chromium alloy, gold-palladium alloy etc. is deposited. For example, there may be used a solution containing a mixture of nickel sulfate, nickel chloride and boric acid in case of nickel plating, and a solution containing a mixture of palladium diaminonitrite, ammonium nitrate and sodium nitrite in case of palladium plating.

The fine particles of the ceramic, which are incorporated into the metal plating solution described above, should have, as one of their properties, a physical and/or chemical bonding easiness with the ceramic to be fused to them by firing. Most desirably, the fine ceramic particles 3 should be identical in composition with the ceramic to be fused thereof. If the fine ceramic particles are not identical in composition with the latter ceramic, it is desirable, in order to attain a firm bond and prevent the ceramic to be fused by firing from break-away, that the thermal expansion factor of the former ceramic be similar to that of the latter ceramic or at least as close as possible.

In general, alumina ($Al_2O_3$), silicon dioxide ($SiO_2$), magnesium oxide ($MgO$), titanium dioxide ($TiO_2$) and the composites thereof, or a ceramic material containing the above oxides or composites are used as the main component of the fine particulate ceramic. The grain size used ranges usually from 5 microns to 100 microns. The amount of the fine particles in the metal plating solution depends upon the field of application for the product, but is usually 500–900 g, preferably 650–850 g, per liter of the metal solution.

If the thickness of the metal plating layer 4 is below ½ of the average diameter of the fine particles of the ceramic, the fine particles 3 may not be firmly fixed to and in the plating layer 4. On the other hand, if the thickness of the metal plating layer 4 is above two thirds of the average diameter of the fine ceramic particles 3 the particles 3 have a reduced area of contact with the ceramic to be fused to them by firing and will not be firmly bonded to the latter ceramic. Therefore, it is preferable that the thickness of the metal plating layer ranges from one half to two thirds of the average diameter of the fine ceramic particles 3.

Figure 2:
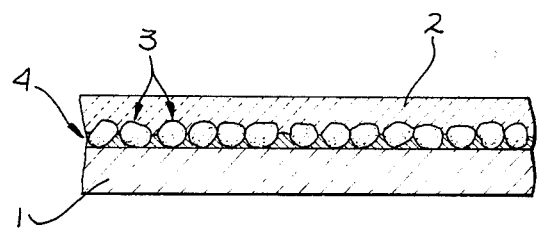
FIG. 2 is an enlarged cross-sectional view of the metal base having the ceramic bonded according to this invention.

Thereafter, a slurry of a second ceramic material 2 forming a second layer is coated on the metal plating layer 4 formed on the base 1 at a desired coating thickness. After drying, the second ceramic layer 2 is fired at a temperature, at which the ceramic layer 2 is fused to the metal, for example, at 940°–970° C. Thus, the ceramic layer 2 is firmly bonded to the metal base 1 as is shown in FIG. 2.

The firm bond appears to be based on the integral structure formed by fusing the fine particles 3 of the ceramic fixed to the metal plating layer 4 and partially projected thereon and the slurry-like coated ceramics during the firing procedure. This bond appears to be based on the physical interaction, in which the ceramics applied in the form of the slurry, layer 2, are engaged with and between the projections of the fine ceramic particles 3 so as to prevent break-away of layer 2 from occurring.

The resulting bond according to the method of this invention and the bond according to the prior art method in which the ceramics are directly fused to the metal were compared with regard to the bonding strength. The following results were obtained.

| Comparison of Bonding Strength ($Kg/cm^2$) (Test method: Shearing test by means of Instron type universal tester) | | |
| --- | --- | --- |
| | Method of this invention | Prior art method |
| 1st test | 351 $kg/cm^2$ | 90 $kg/cm^2$ |
| 2nd test | 356 | 133 |
| Average | 353.5 | 111.5 |

As is apparent from the above data, the bond according to the method of this invention has a bonding strength of three times or more of that according to the prior art method. Furthermore, the prior art method results in a large and wide scattering of the bonding strength data (numerical data), while the scattering of the bonding strength data according to the method of this invention occurs only in a narrow scope and is constant. In addition, the bonding strength data according to the method of this invention do not depend on the type of character of the matrix metal 1.

The production of the prosthetic teeth according to the method of this invention is described hereinbelow.

First, a metal crown for a prosthetic tooth is prepared by pressing or casting. This metal crown is made of metal or alloy, such as gold, palladium, gold-palladium alloy, nickel-chromium alloy and the like.

In this embodiment, the metal crown is prepared from a nickel-chromium alloy consisting of 82% of nickel, 10% of chromium, 5% of molybdenum, 1.8% of beryllium and 1.2% of the other metals, all percents are by weight.

Figure 3:
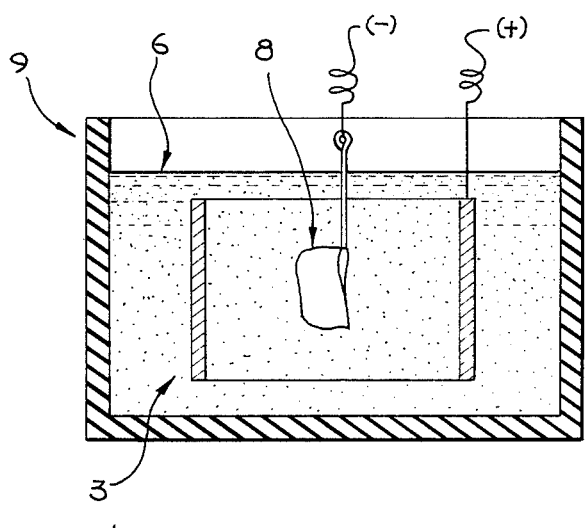
FIG. 3 is a cross-sectional view for illustrating the process of plating on the surface of the metal crowns for prosthetic teeth in the method of this invention.
Figure 4:
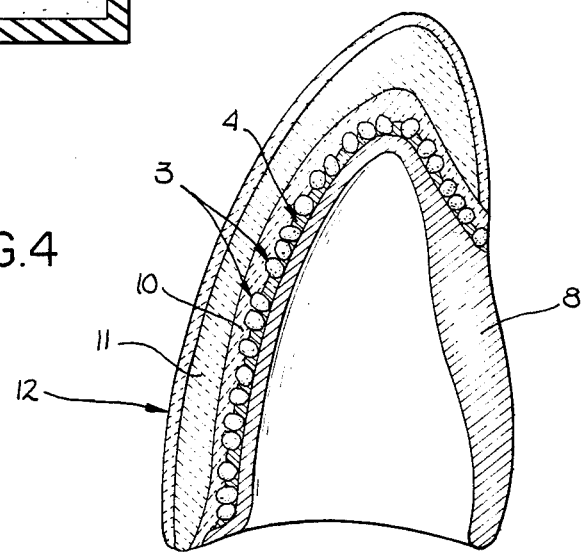
FIG. 4 is a cross-sectional view of an embodiment of the prosthetic tooth produced according to the method of this invention, and each of FIGS. 5, 6, 7 and 8 represents a ready-made prosthetic tooth produced according to the method of this invention. In each of these drawings, a left-hand view (a) is a front view of the tooth, a central view (b) is a central cross-sectional view of the tooth and a right-hand view (c) is a perspective view of the tooth.

Then, as is shown in FIG. 3, a palladium plating material containing the fine ceramic particles 3 are charged into a plating tank 9. The plating is carried out by connecting a pole plate 7 to an anode and the metal cast crown 8 to a cathode, respectively. As is shown in FIG. 4, the numerous fine ceramic particles 3 adhere to the surface of the cast metal crown 8, and palladium is deposited in the space between the fine ceramic particle 3. The thickness of the plating layer 4 increases with the lapse of time and after sufficient time the plating layer is thick enough to fix the fine ceramic particles 3 therein.

When the plating layer 4 achieves a thickness of about one half to one third of the average diameter of the fine ceramic particles 3, the plating is stopped and the cast metal crown 8 is removed from the plating tank 9 and washed. By washing, only the fine ceramic particles directly fixed to the surface of the cast metal crown 8 through the plating layer 4 remain from the numerous fine particles of the ceramics adhered to layer 4. In this manner, the heads of the fine particles 3 are sufficiently projected from the plating layer, while the other less adherent fine particles are removed. In the plating step, a part of the crown in which the plating is not required, is protected by application of an insulating coating similarly to the case of the conventional plating.

Thereafter, the opaque porcelain 10 is applied forming the primary plating layer and then fired. The result is shown in FIG. 4 in the partial cross-sectional view. The depressions between the projections of the fine ceramic particles 3 over the plating layer 4 are filled in with the opaque porcelain layer 10. The opaque porcelain layer 10 is thus engaged with the projections to give the firm bond physically, and also chemically, if the fine ceramic particles 3 of the same type as the opaque porcelain layer 10 are used at least in part. The coating and firing of the dental crown colored porcelain layer 11 and the enamel ceramic layer 12 on the surface of the opaque porcelain 10 are carried out in a conventional manner. Since each of the opaque porcelain layer 10, the dental crown colored porcelain layer 11 and the enamel porcelain 12 is composed of a ceramic of the same type (i.e., containing alumina and silicon dioxide as the main part), their bonded surface will not be easily broken away.

When particles of alumina having a thermal expansion factor of $7 \times 10^{-6}/°C.-14 \times 10^{-6}/°C.$ are used as the fine ceramic particles 3 incorporated into the metal plating solution, a bond can be obtained without influences of the thermal expansion and the contraction, since the above opaque porcelain layer 10 generally has a thermal expansion factor of $12 \times 10^{-6}/°C.-13 \times 10^{-6}/°C.$ The method of bonding metal and ceramic according to this invention can be applied to prosthetic teeth with various shapes other than those shown in FIG. 4.

For example, FIG. 5 to FIG. 8 each represents a different embodiment of so-called ready-made prosthetic teeth which are standardized in size and shape. In these embodiments, a metal material is pressed or cast to form the metal crown 21 having depressions and projections integral therewith, which are used to set it. The dental crown colored porcelain 23 is fused to the formed metal crown 21 by firing.

In order to firmly bond the dental crown colored porcelain 23, i.e., an inorganic material to the metal crown 21, the surface of the plating layer 22 of a non-oxidizable metal such as gold or palladium is roughened by attachment of the numerous fine ceramic particles such as alumina, from one half to one third of the average diameter particles over the surface of the plating layer 22. The dental opaque porcelain (not shown) and the dental crown colored porcelain 23 are then successively coated, and subsequently fired at atmospheric pressure or under reduced pressure of 65-70 cmHg in an electric furnace. In this manner, both physical and chemical bonds are attained and the desirable bonding strength obtained.

The material suitable for a metal crown 21 is a non-oxidizable metal such as gold, palladium. However, since these noble metals are very expensive and in short supply, a nickel-chromium alloy is used in order to produce prosthetic teeth at lower cost.

The above prosthetic teeth of this invention have the following advantages:

(1) The bond of a metal crown and a ceramic has a bonding strength of three times or more of that of a bond according to the prior art method, and the prosthetic teeth can be semipermanently used without break-away of the ceramic.
(2) The prosthetic teeth are strong and hard to damage, since porcelain is fused in a thin and uniform layer to a metal crown.
(3) The prosthetic teeth are very light, since their thickness is reduced to 1.5-1.7 mm, while that of the prior art is 4-5 mm. Particularly in case of complete or full upper denture, the denture is rarely dislocated, since the denture is light weight.
(4) Technical works can be easily carried out, since the prosthetic teeth have excellent strength.
(5) So-called stain works for correcting the tone of the teeth can be easily carried out, and individual tones can be easily adjusted.
(6) Metal crowns can be produced at less cost by using a nickel-chromium alloy.
(7) The prosthetic teeth have excellent service durability, since they can be firmly fitted to a dental plate by the depressions and projections which are integrally formed in the metal crown.
(8) Various arrangements can be easily achieved, since thin prosthetic teeth can be produced.

While the invention has been shown and described with reference to a preferred embodiment thereof, it will be obvious to those skilled in the art that various changes and modifications may be made therein without departing from the scope of the invention as defined by the following claims.

What is claimed is:

1. A method of firmly bonding an opaque porcelain to a metal crown for prosthetic teeth comprising the steps of:
   plating the metal crown with a plating solution containing metal ions and fine ceramic particles dispersed therein to form a composite layer on the metal crown, said composite layer comprising a metal layer on the surface of the metal crown having plurality of fine ceramic particles embedded in the metal layer and partially projecting above the metal layer;
   applying the opaque porcelain to the composite layer; and
   firing the porcelain to fuse it to the composite layer and thereby to the metal crown.

2. A method according to claim 1, wherein the thermal expansion factor of the fine ceramic particles approximates that of the second opaque porcelain layer.

3. A method according to claim 1, wherein the metal crown for the prosthetic teeth is made of a nickel-chromium alloy.

4. A method according to claim 1, wherein the metal crown for the prosthetic teeth has means for fitting.

5. A prothetic tooth produced according to the method of claim 1, the tooth consisting of a metal crown, a metal plating layer having a plurality of fine ceramic particles embedded therein and partially projecting therefrom formed on the metal crown, and an opaque porcelain layer bonded to the metal plating layer.

6. A prosthetic tooth produced according to the method of claim 2, the tooth consisting of a metal plating layer having a plurality of fine ceramic particles embedded therein and partially projecting therefrom formed on the metal crown, and an opaque porcelain layer bonded to the metal plating layer.

7. A prosthetic tooth produced according to the method fo claim 3, the tooth consisting of a metal plating layer having a plurality of fine ceramic particles embedded therein and partially projecting therefrom formed on the metal crown, and an opaque porcelain layer bonded to the metal plating layer.

8. A prosthetic tooth produced according to the method of claim 4, the tooth consisting of a metal plating layer having a plurality of fine ceramic particles embedded therein and partially projecting therefrom formed on the metal crown, and an opaque porcelain layer bonded to the metal plating layer.

9. A prosthetic tooth consisting of a metal crown, a metal plating layer having a plurality of fine ceramic particles embedded therein and partially projecting therefrom formed on the metal crown and an opaque porcelain layer bonded to the metal plating layer.

* * * * *